Figure 1:
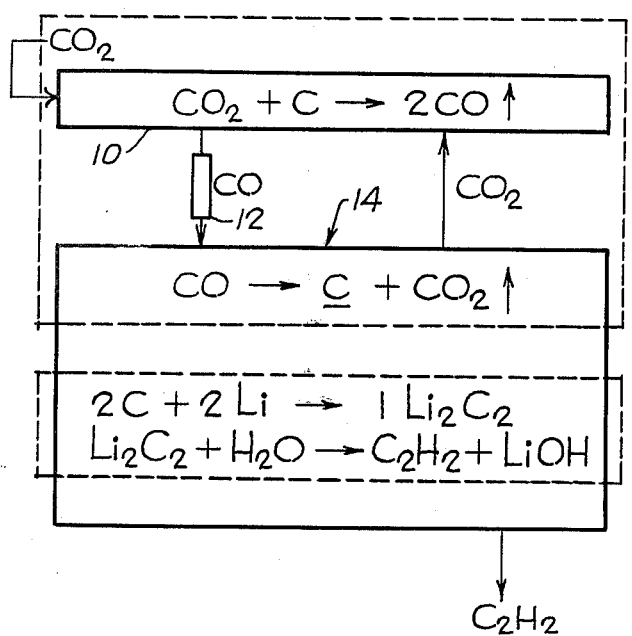

United States Patent [19]

Tamers

[11] 4,128,624
[45] * Dec. 5, 1978

[54] METHOD FOR INTRODUCING CARBON INTO EVACUATED OR PRESSURIZED REACTION VESSELS AND REACTION PRODUCTS THEREFROM

[76] Inventor: Murry A. Tamers, 14131 Cypress Ct., Miami Lakes, Fla. 33014

[*] Notice: The portion of the term of this patent subsequent to Feb. 22, 1994, has been disclaimed.

[21] Appl. No.: 623,943

[22] Filed: Oct. 20, 1975

Related U.S. Application Data

[63] Continuation-in-part of Ser. No. 572,165, Apr. 28, 1975, Pat. No. 4,009,219.

[51] Int. Cl.² .............. C01B 31/30; C01B 31/02; C09C 1/48
[52] U.S. Cl. .................. 423/439; 423/449; 423/459; 423/461
[58] Field of Search .......... 423/439, 459, 247, 4, 423/449

[56] References Cited

U.S. PATENT DOCUMENTS

| | | | |
|---|---|---|---|
| 1,904,585 | 4/1933 | Willekens | 423/459 |
| 1,964,744 | 7/1934 | Odell | 423/459 |
| 2,642,347 | 6/1953 | Gilbert | 423/439 |
| 2,716,053 | 8/1955 | Mayland | 423/459 |
| 2,802,723 | 8/1957 | Lemke | 423/439 |
| 3,371,996 | 3/1968 | Hibshman | 423/459 |
| 3,714,323 | 1/1973 | Dolci et al. | 423/459 |
| 3,758,673 | 9/1973 | Buben et al. | 423/656 |
| 3,842,159 | 10/1974 | Niebylski et al. | 423/213.5 |
| 3,861,885 | 1/1975 | Schora | 423/459 |

FOREIGN PATENT DOCUMENTS

| | | | |
|---|---|---|---|
| 117609 | 5/1930 | Austria | 423/459 |
| 1388061 | 3/1975 | United Kingdom | 423/656 |

OTHER PUBLICATIONS

Tamers, M. A., Sensitivity enhancement for low level activities by complete synthesis of liquid scintillation soluents, Molecular Crystals 1968, vol. 4, pp. 261-276.

*Primary Examiner*—O. R. Vertiz
*Assistant Examiner*—Gary P. Straub
*Attorney, Agent, or Firm*—McDougall, Hersh & Scott

[57] ABSTRACT

A method for introducing ash-free solid carbon into a reaction vessel while under pressure or vacuum conditions and the conversion of said carbon to a metal carbide for the production of acetylene for use as such and as a precursor in the preparation of other organic compounds. The technique is also used for de-ashing and desulfurizing coal or char and is a method for extracting carbon from any charable substance, including wastes. It is, in addition, used as a method of exploiting the gases evolved from underground carbonaceous deposit fires.

20 Claims, 2 Drawing Figures

METHOD FOR INTRODUCING CARBON INTO EVACUATED OR PRESSURIZED REACTION VESSELS AND REACTION PRODUCTS THEREFROM

This is a continuation-in-part of my copending application Ser. No. 572,165, filed Apr. 28, 1975, and entitled "The Total Synthesis of Benzene from Non-Hydrocarbon Materials" now U.S. Pat. No. 4,009,219, issued Feb. 22, 1977.

This invention relates to a method and means for making solid carbon, especially ash-free, available as a reactant in a closed system operating under vacuum or pressure conditions and it relates further to the utilization of the method and means for carbon introduction in a continuous process for the preparation of metal carbides from a non-hydrocarbon source or coal which, by comparison with liquid or gaseous hydrocarbons, are readily available in relatively unlimited supply and at low cost. It is also used as a method for extracting or concentrating carbon from or in any charable substance.

One of the principal problems encountered in the engineering and design of a continuous process, in which elemental carbon or coke or other chars are utilized as reactants in an evacuated or in a pressurized reactor vessel, is the introduction of such solid substances and the extraction of any ash that is formed without drastically changing the particular pressure or removing the vessel lid.

No practical means or method has heretofore been made available in chemical processes for the introduction of elemental carbon into a reaction vessel operating continuously under pressure or vacuum conditions. Ordinarily the introduction of such solids requires opening of the vessel or connecting chamber to atmospheric conditions and air for the introduction of solid elemental carbon particles followed by re-establishment of the desired level of pressure or vacuum before re-entry of the reaction vessel into the reaction cycle and exclusion of air contamination. This not only allows for introduction of considerable foreign material, including air, into the reaction vessel, but it requires removal and regeneration of the vacuum or pressure conditions, with its consequent costs and interference with the continuity of the chemical process, and corresponding loss of time and possibly yield.

It is an object of this invention to provide a method and means for the introduction of elemental solid carbon particles as a reactant in a reaction vessel operating under pressure or vacuum conditions, and it is a related object to form such elemental carbon in situ within the reaction vessel without drastic disturbance of the reaction conditions, without interruption of the chemical process, and without the introduction of foreign substances that might interfere with the reaction or bring about undesirable side reactions, in which such elemental carbon is made available from raw materials which are in extensive supply and at low cost, by comparison with other carbon source, such as liquid and gaseous hydrocarbons or their derivatives which are in diminishing supply and of increasing cost.

Figure 2:
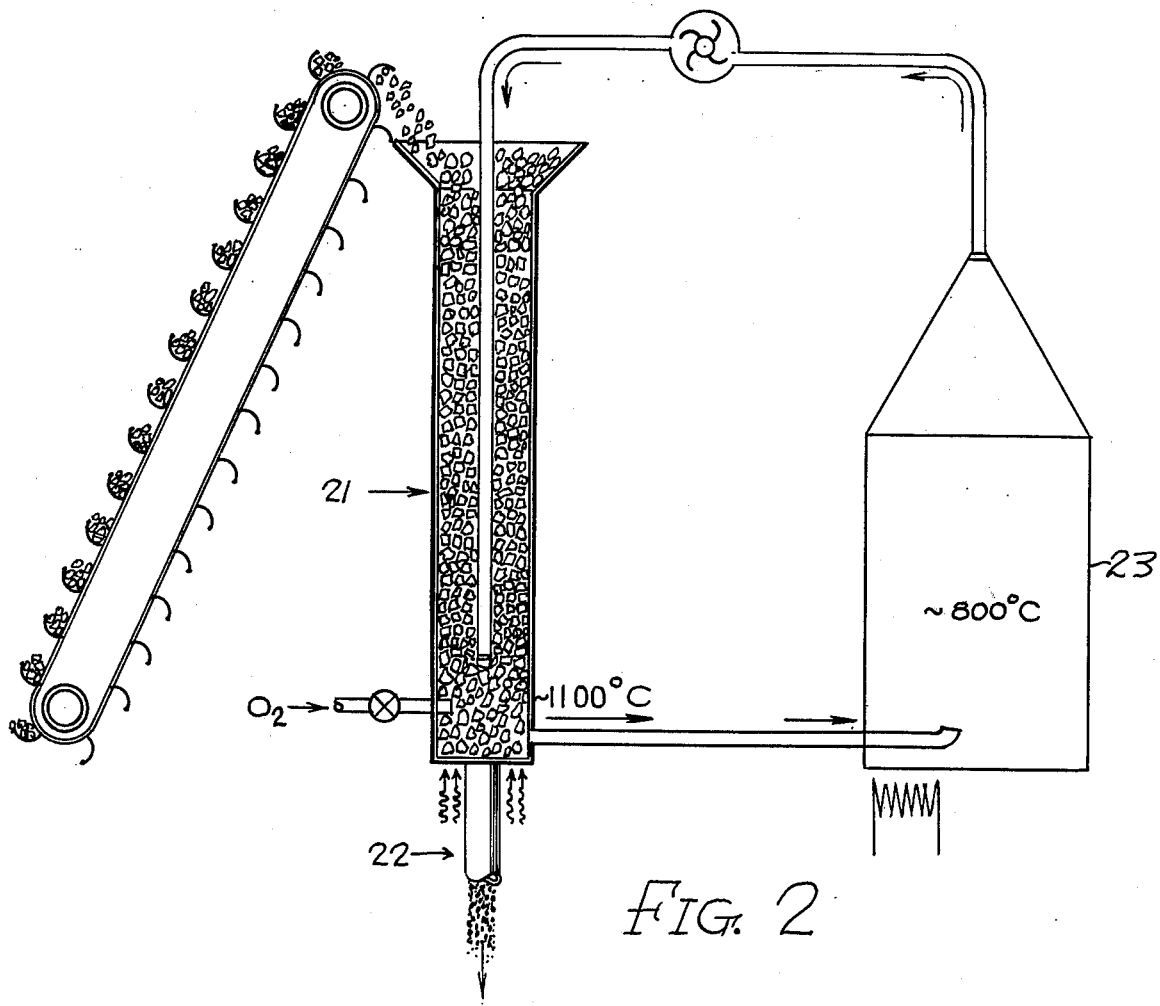

FIG. 1 is a schematic diagram of the reactions which take place in accordance with the practice of the invention, and FIG. 2 is a schematic elevational view of an apparatus for carrying out the reactions.

An important concept of this invention resides in the discovery that carbon monoxide can be introduced in gaseous state into the reaction vessel operating under vacuum or pressure conditions for conversion in situ within the vessel at elevated temperature, preferably in the presence of a suitable catalyst, to solid elemental carbon in a highly reactive nascent state for chemical reaction of the carbon that is formed. Carbon monoxide can be introduced into the reaction vessel while it is under the vacuum or pressure conditions and the carbon monoxide introduced can be reduced to elemental carbon without disruptive changes of the pressure or vacuum conditions, as the case may be, in the reactor or connecting chambers. The elemental carbon that is freshly formed in situ by conversion of the carbon monoxide to carbon and carbon dioxide, in accordance with the following equation, is more or less in the highly reactive nascent state, a state most suitable for subsequent chemical reaction. It is, in addition, ash-free. The carbon dioxide by-product is gaseous and, thus, conveniently removed from the reactor.

$$2\,CO \rightarrow C + CO_2 \tag{1}$$

The reaction is a reversible reaction and the equilibrium can be driven in the direction to maximize utilization of carbon monoxide and the production of elemental carbon by pressurizing the reactor with carbon monoxide and/or by providing a component which either reacts with the carbon dioxide that is formed, such as in the use of lithium oxide as a conversion catalyst and as a reactant which takes up carbon dioxide, or by the use of a material which absorbs carbon dioxides, such as lithium oxides or hydroxides.

Carbon dioxide, available from the hot gaseous waste from the reaction of carbonates in the lime or cement industry or from stack gases which are otherwise exhausted into the atmosphere, or from gases given off during fermentation, or otherwise made available from calcium or other carbonates, which are in endless supply at low cost, can be used as the source for the reaction to produce carbon monoxide in the reaction vessel.

For this purpose, the carbon dioxide is reacted with carbon outside of the reaction vessel for conversion of the carbon dioxide to form carbon monoxide in accordance with the following equation:

$$CO_2 + C \rightarrow 2\,CO \tag{2}$$

This permits the economy of a substantially self-sustaining cycle wherein the carbon dioxide that is made available in the reaction vessel from the conversion of carbon monoxide to elemental carbon, in accordance with equation (1) for use in the reaction with elemental carbon outside of the reaction vessel, in accordance with equation (2) to make carbon monoxide available for introduction into the reaction vessel, in accordance with equation (1). Thus elemental carbon outside of the reactor is carried into the reactor from an intermediate gaseous state, while the carbon dioxide cycles between the formation of elemental carbon in the reactor to reaction with the elemental carbon outside of the reactor to make carbon monoxide available for use in the reactor.

The described reactions are somewhat temperature dependent. Reaction (2), for making carbon monoxide available from carbon dioxide and carbon, is usually performed at a temperature above 800° C. and preferably at a temperature within the range of 1000° to 1250° C. Reaction (1), for conversion of carbon monoxide to elemental carbon and carbon dioxide, is carried out at a temperature within the range of 400° to 900° C. When lithium oxide or hydroxide is present, the reaction that occurs with carbon dioxide enables a lower temperature, such as a temperature within the range of 400° to 600° C., to be employed in reaction (1).

Coal, coke, other chars, and chars of all municipal, agricultural, industrial, or forestry waste products can also be utilized to produce carbon monoxide. They can be burned directly in limited oxygen. Also, the FIG. 2 shows an example of another possible arrangement. Here the feedstock material is fed on top of the reaction tube and descends by gravity to the heated chamber 21. Ashes leave the system through a grating at 22. The carbon dioxide gas initially produced is passed through the heated zone and reaches a temperature of approximately 1100° C. Under these conditions, the high temperature and the presence of elemental carbon, the carbon dioxide reacts largely to form carbon monoxide. This gas is then passed to the reactor vessel and cooled therein. It decomposes to some extent to deposit carbon in the vessel 23. The regenerated carbon dioxide with some remaining carbon monoxide is recycled to the heated chamber for reconversion to carbon monoxide.

To the carbonaceous feedstock can be added a small amount of limestone or other carbonate, for example, about 0.5%. This decomposes in the region directly above the intensely heated zone to produce an excess of carbon dioxide. Heat can be supplied by burning fossil fuels, electricity, direct heat from nuclear reactors or waste heat from other industrial processes. This carbon dioxide escapes through the descending feedstock, thereby removing air trapped between the particles. It also provides a positive pressure to prevent air from entering from the ashes gate. Instead of the carbonate method of air exclusion, some oxygen can be fed into the intensely heated zone to burn a small amount of the feedstock, creating in this way the excess carbon dioxide as well as additional heat.

Raw coal and other solid substances with volatile components can be used as the raw materials for the carbon monoxide generation, as well as for direct reaction in the total benzene or acetylene synthesis of the previous application, Ser. No. 572,165 now U.S. Pat. No. 4,009,219. In these cases the feedstock is carbonized by some operation in the process itself. For the system of FIG. 2, the carbon dioxide evolving from the feedstock stack top pushes the gases evolved from the coal, for example, into a scrubber where coal tar liquids are collected and then to a gas separation device for recovery of hydrogen and other valuable gases. The coal or other feedstock material is dried in the stack.

Another excellent source of carbon monoxide is underground coal seam or other natural hydrocarbon fires. If oxygen, oxygen enriched air, or air is pumped into the fire, large amounts of carbon monoxide can be extracted at another location. The reducing atmosphere of the fire causes most of the sulfur to remain behind. The evolved carbon monoxide can be obtained hot, which is useful to prevent decomposition before transport into the reaction chamber and as a heat source. Both intentionally ignited and previously burning systems can be used. Likewise, fires can be set in abandoned mines to burn the coal or other carbonaceous material left behind from the mining operation. Often this constitutes the roof supporting pillars. Coal seams that are too thin or too deep for normal mining can be exploited in this process.

In some processes, carbon monoxide may be produced in succeeding reactions. This is fed directly into the reactor or the circuit. For example, in the case where the carbon deposited is being used to reduce a metallic oxide, such as lithium oxide, carbon monoxide is evolved at high temperatures, about 1300° C., during the reduction. This carbon monoxide would be fed directly into the carbon monoxide generator of another circuit. It would there contribute its heat and pass into the circuit line. The temperature of the carbon monoxide available will determine at what position it is fed into a circuit. Reactions (4) and (6) discussed later are examples of such a situation.

The invention will be illustrated by reference to its use in the preparation of valuable organic carbonaceous products from non-hydrocarbon sources or coal, which are in substantial supply, at low cost. This includes coke or chars made from coal or other solid hydrocarbons even when the coke or chars are considered intermediate stages and the coal, for example, the original raw material. A representative of the organic carbonaceous materials that can be produced are acetylene to be taken as such or from which benzene, ethane, ethylene and other saturated and unsaturated organic compounds can be synthesized. Representative of the plentiful supply of low cost raw material which may be utilized in the preparation of such more valuable organic carbonaceous products are the materials previously described as a source for elemental carbon, including carbonates and other carbon containing compounds and ores.

In my copending application Ser. No. 572,165 now U.S. Pat. No. 4,009,219, description is made of the formation of a metal carbide by reaction of an alkali metal, such as sodium, potassium, cesium, and preferably lithium, their oxides or hydroxides, or an alkaline earth metal such as barium, calcium, strontium and the like, or their oxides or hydroxides, with elemental carbon at elevated temperature and the reaction of the formed metal carbide with water to yield acetylene and the oxide of the metal. Carbonates can also be used directly. The acetylene produced can be subjected to conventional polymerization, hydrogenation, chlorination, oxychlorination, and the like reactions, which are well known in the chemical art to produce such desirable compounds as ethylene, ethane, vinyl chloride, benzene and the like saturated and unsaturated, halogenated or unhalogenated organic carbonaceous alkyl or alkaryl compounds, as well as many other organic compounds obvious to the skilled in the art.

EXAMPLE 1

In FIG. 1, carbon dioxide, derived from the calcination of calcium carbonate, flue gas, fermentation off gas or the like by-product gases, is passed over charcoal in a closed retort 10 heated to a temperature of about 1100° C. to convert carbon dioxide to carbon monoxide, in accordance with the reaction of equation (2).

The effluent gas, containing carbon monoxide in admixture with a small percentage of unreacted carbon dioxide, is cooled by passage through heat exchanger 12 to a temperature of about 700° C. upon introduction into a stainless steel reaction vessel 14, containing lithium oxide or hydroxide or other catalytic agents. The reaction vessel is maintained at a temperature of about 700°-900° C., with the exclusion of air, to maintain non-oxidizing conditions. Under such conditions, the carbon monoxide is partially converted by reaction to elemental carbon and carbon dioxide, in accordance with equation (1).

A closed system is maintained between the outlet from the reactor 14 to the inlet to the retort 10 for cycling the carbon dioxide generated from the monoxide in the reactor 14 to the retort 10 for use in the reaction with carbon to generate carbon monoxide, and for cycling the carbon monoxide from the retort 10 to the reactor 14 for use in the reaction to generate carbon with the gaseous carbon dioxide as a by-product. The cycle is maintained with the possible addition of carbon dioxide and carbon to the retort 10 until the desired amount of elemental carbon has been produced in the reactor 14.

At this stage, any one of the reactions (A) or (G), described in the aforementioned copending application Ser. No. 572,165 now U.S. Pat. No. 4,009,219, can be carried out in the reactor 14 without interrupting the reaction conditions, namely (A) $2Li + 2C \rightarrow Li_2C_2$ (3)

(B) $10Li + 2CO_2 \rightarrow Li_2C_2 + 4Li_2O$ (C) $6Li + 2CO \rightarrow Li_2C_2 + 2Li_2O$ (D) $10Li + 2CaCO_3 \rightarrow Li_2C + 4Li_2O + 2CaO$ (E) $Li_2O + 5CO \rightarrow Li_2C + 3CO_2$ (F) $2LiOH + 5CO \rightarrow LI_2C_2 + Li_2C_2 + 3CO_2$ (G) $Li_2O + 3C \rightarrow Li_2C_2 + CO$ (4)

Instead of making use of the metal or its oxides, use can be made of the hydroxide, which will be reduced to the oxide at the reaction temperature. Use can also be made of the metal carbonate which will be reduced to the oxide, under reaction conditions, in accordance with the following equation, for example:

$$Li_2CO_3 \rightarrow Li_2O + CO_2 \quad (5)$$

The above reaction readily occurs at temperatures of 600°–1000° C. and is best carried out under vacuum conditions with continuous removal of the carbon dioxide.

In the presence of elemental carbon, the oxide will automatically be reduced to the metal in accordance with the following equation:

$$Li_2O + C \rightarrow 2Li + CO \quad (6)$$

This reaction generally takes place at a temperature within the range of 1000°–1300° C., under vacuum conditions, with continuous removal of the carbon monoxide. The carbon monoxide and the carbon dioxide gases that are given off can be extracted from the reactor for use, as in equations (1) or (2).

As a result, it can be projected that the principal reaction is that corresponding to equation (3), with reactions such as identified as reactions (B), (C), (D), (E), (F) and (G) in the aforementioned copending application, occurring in small part when carbon dioxide and/or carbon monoxide are caused to be present from the conversion of the metal carbonate.

When the carbon in sufficient amount has been deposited in the reactor, the flow of carbon monoxide is terminated, the reactor is evacuated and the materials heated to a temperature of about 1300° C. for 2 hours or more with the continuous removal of any gases evolved during the reaction. This initial reaction at about 1300° C. is followed by reaction for 1 hour or more at about 950° C.

To convert the formed lithium carbide to acetylene by hydrolization with water, in accordance with the following equation $$Li_2C_2 + 2H_2O \rightarrow C_2H_2 + 2LiOH \quad (7)$$

the reaction products are cooled to 0°–150° C. and hydrolyzed with water to form the acetylene gas which is vented off as product, while the residual lithium hydroxide can be allowed to remain in the reactor for use as a catalyst in a new cycle of operation. Hydrogen, which may come off as a by-product with acetylene, especially when excessive amount of metal is present, can be easily separated from the acetylene by well known conventional techniques.

The acetylene is a raw material which may be used in the synthesis of a number of valuable organic hydrocarbons, such as ethane, ethylene, vinyl chloride, benzene, and the like.

A more detailed description, by way of an example of the preparation of lithium carbide by reaction of the elemental carbon in Example 1 and the subsequent conversion of the formed lithium carbide to acetylene, will now be given.

EXAMPLE 2

12.5 grams of elemental carbon and 7.1 grams of lithium metal were heated in the evacuated container for 30 minutes at about 1000° C. The carbon and lithium metal reacted, under the nonoxidizing conditions prevailing, to form lithium carbide in accordance with the reaction (3). The reaction vessel was cooled to about ambient temperature and water was introduced in the molar ratio of 2 moles of water ± 10% per mole of lithium carbide to convert the lithium carbide by hydrolysis to acetylene. 11.1 liters of acetylene was obtained.

As described in my aforementioned copending application, while it is preferred to make use of lithium as the reactant with the elemental carbon, the lithium metal can be substituted in whole or in part, in Example 2, with another alkali metal such as sodium, potassium, or cesium, or by an alkaline earth metal such as calcium, barium, strontium, and the like.

In order to effect optimum efficiency from the standpoint of metal utilization, it has been found that it is desirable to minimize side reactions which tend to consume metal. Such metal consuming side reactions have been found to occur from utilization of carbon having a high degree of impurities, such as a high ash content carbon. Such metal consuming side reactions appear to be completely avoided when, in accordance with the practice of this invention, the reactive carbon is made available by conversion from carbon monoxide, in accordance with the practice of this invention, to provide a highly reactive elemental carbon, which is in the nature of a nascent carbon which reacts in a manner to be relatively free of metal consuming side reactions. Hydrogen, oxygen and nitrogen should be held to a minimum in the reaction vessel for most efficient utilization of the raw materials.

In order to assure consumption of the entire increment of metal in the reaction, it is sometimes desirable to make use of the metallic component in an amount slightly less (up to 10% less) than the stoichiometric amount for reaction with the carbon to produce the metal carbide. When the metal is present in an amount in excess of that required to react with the carbon in the formation of the metal carbide, the excess metal reacts during subsequent hydrolyzation of the carbide to produce hydrogen gas. While such hydrogen gas has economic value, it is desirable, from the standpoint of the continuity of the process, to minimize such side reactions.

The metal carbide forming reaction (3) is exothermic and spontaneous and is carried to completion at 1000° C. Higher temperatures can be used with less reactive metals such as the alkaline earth metal carbides.

In the hydrolysis reaction, the water or steam can be added directly to the lithium carbide thereby to enable the reaction to be carried out in the reaction vessel in which the carbide is formed, if desired. This enables a continuous operation from carbide formation to the formation of acetylene. In the event of the formation of the carbide of an alkaline earth metal, hydrolysis can be carried out in the same vessel by the addition of water, but it is preferred to transfer the formed carbide to another locality where it can be broken up into small segments for addition to the water.

After hydrolysis of the carbide to produce acetylene, which is removed as a gas, the solid metal hyrdoxide that remains can be converted back to the metal for use as the reactant with the carbon in equation (3) by reaction with hydrochloric acid and decomposing the chloride, as by fused salt electrolysis to the metal, or use can be made of the metal oxide as the catalyst for conversion of the carbon monoxide to carbn and for subsequent reaction with the formed carbon in metal carbide formation, as described in my copending application, by way of the following equation:

$$Li_2O + 3C \rightarrow Li_2C_2 + CO \tag{8}$$

The hydroxide is converted to the oxide by thermal decomposition under vacuum.

It will be apparent from the foregoing that there is provided a means for making elemental carbon available as a reactant in a reaction vessel operating under pressure or vacuum conditions whereby the carbon that is formed is in a purified and reactive state and wherein the means described can be tied into a continuous operation for the production of acetylene and various carbonaceous products therefrom by the use of readily available sources of carbon containing compounds.

The material that will be eventually reacted with the deposited carbon is present in the reactor during the carbon monoxide decomposition. Although it might initially act as a catalyst for the decomposition, it is rapidly covered with the carbon black. The deposited carbon black also catalyzes the further decomposition of the carbon monoxide entering the reactor.

The velocity of the gases pumped through the circuit is determined by the rate of carbon monoxide decomposition. It is not recommended to wait for the majority of the carbon monoxide in the reactor to come to thermodynamic equilibrium at the reactor temperature with carbon and carbon dioxide. The gas being pumped out of the reactor will still have a larger carbon monoxide percentage than the equilibrium percentage. A compromise must be made between waiting for carbon monoxide decomposition completion and regeneration of additional carbon monoxide in the carbon monoxide generator.

It will be further apparent that the process described represents a regenerative process wherein reaction products are recycled for utilization as reactive components in the reaction with the result that it becomes possible to produce acetylene as a product from a feed of non-hydrocaron material with acetylene being capable of utilization as a precursor in the preparation of valuable hydrocarbon products It will be further apparent that the process described here can be used as a method of desulfurizing and deashing coal or any wastes or any other carbonaceous materials that can be charred. It can be utilized, also, as a means of concentrating carbon in charable materials. In the reducing atmosphere produced by the carbon monoxide generation by passing carbon dioxide over the char feedstock, metal ion-containing ash remains behind, along with much of the sulfur. The volatile sulfur produced is either elemental or in the form of hydrogen sulfide, both of which are easily removed from the carbon monoxide stream. The carbon monoxide serves as an intermediate gaseous state that consumes impure solid carbon and precipitates pure carbon, with very high material efficiencies. Thermal losses can be minimized by using the heat removed from the carbon monoxide to pre-heat the incoming carbonaceous feedstock.

It will be further apparent that the carbon produced by the process described here can be used as a combustible fuel. It can be oxidized in air or oxygen or oxygen enriched gas to provide heat, electricity, an expanded gas, or pressure.

It will be further apparent that coal and all other solid hydrocarbons are readily carbonized to coke and are, therefore, excellent raw materials for these processes.

It will be understood that changes may be made in the details of formulation and operation without departing from the spirit of the invention, especially as defined in the following claims.

I claim:

1. The method for introducing elemental carbon in solid form in a reaction vessel operating under pressure other than atmospheric and reacting the carbon that is formed to a metal carbide comprising introducing carbon monoxide in a gaseous state under the pressure conditions existing within the reactor and thermally converting said carbon monoxide in the presence of lithium, its oxide or hydroxide as the catalyst at a temperature within the range of 400–900° C. to elemental carbon and carbon dioxide under non-oxidizing conditions existing within the reactor, and removing carbon dioxide that is formed, leaving the elemental carbon in solid form as a reactant, reacting the carbon with lithium along or with lithium in combination with other alkali or alkaline earth metals at a temperature within the range of about 700°–1000° C. to form the corresponding carbides.

2. The method as claimed in claim 1 in which the carbon monoxide is converted to solid elemental carbon and gaseous carbon dioxide at a temperature of about 500° C.

3. The method as claimed in claim 1 in which the carbon monoxide gas is generated outside of the reactor by reacting solid carbon with carbon dioxide at elevated temperature, under non-oxidizing conditions.

4. The method as claimed in claim 3 in which the reaction of solid carbon with carbon dioxide is carried out at a temperature above 800° C.

5. The method as claimed in claim 3 in which the reaction of solid carbon with carbon dioxide is carried out at a temperature within the range of 1000°-1250° C.

6. The method as claimed in claim 3 in which the carbon dioxide resulting from the reaction of carbon monoxide in the reaction vessel is recycled as carbon dioxide feed for reaction with carbon outside of the vessel and the carbon monoxide generated by reaction of said carbon and carbon dioxide outside of the vessel is cycled to the reaction vessel for conversion into carbon and carbon dioxide.

7. The method as claimed in claim 6 in which the minor amounts of carbonates such as limestone are added to the carbonaceous feedstock in order to produce excess carbon dioxide gas to purge air and other volatiles from the entering feedstock material.

8. The method as claimed in claim 6 in which small amounts of oxygen gas are fed into the intensely heated zone of the carbonaceous feedstock in order to produce excess carbon dioxide to purge air and other volatiles from the entering feedstock material.

9. The method as claimed in claim 6 in which coal or other carbonaceous feedstock containing valuable volatilizable substances is used and the resultant volatiles are collected.

10. The method as claimed in claim 1 in which the carbon monoxide is generated in underground coal mines or deposits or other natural carbonaceous seams by purposefully igniting a fire, feeding said with pumped oxygen, air, or oxygen enriched air, and extracting a gas rich in carbon monoxide.

11. The method as claimed in claim 10 in which already burning underground carbonaceous seams or deposits are used for the carbon monoxide production.

12. The method as claimed in claim 1 in which the carbon is waste materials from municipal, industrial, agricultural, forestry and other sources.

13. The method for introducing elemental carbon in solid form in a reaction vessel operating under pressure other than atmospheric and reacting the carbon that is formed to a metal carbide comprising introducing carbon monoxide in a gaseous state under the pressure conditions existing within the reactor and thermally converting said carbon monoxide in the presence of lithium, its oxide or hydroxide as the catalyst at a temperature within the range of 400-900° C. to elemental carbon and carbon dioxide under non-oxidizing conditions existing within the reactor, and removing carbon dioxide that is formed, leaving the elemental carbon in solid form as a reactant, reacting the carbon with lithium oxide or lithium hydroxide first at a temperature within the range of 1000-1300° C. for a period of time sufficient to reduce said lithium oxide or lithium hydroxide to lithium metal and then reacting said lithium metal at a temperature within the range of 700-1000° C. to form lithium carbide.

14. The method as claimed in claim 13 in which the carbon monoxide is converted to solid elemental carbon and gaseous carbon dioxide at a temperature of about 500° C.

15. The method as claimed in claim 13 in which the carbon monoxide gas is generated outside of the reactor by reacting solid carbon with carbon dioxide at elevated temperature, under non-oxidizing conditions.

16. The method as claimed in claim 15 in which the reaction of solid carbon with carbon dioxide is carried out at a temperature above 800° C.

17. The method as claimed in claim 15 in which the reaction of solid carbon with carbon dioxide is carried out at a temperature within the range of 1000-1250° C.

18. The method as claimed in claim 15 in which the carbon dioxide resulting from the reaction of carbon monoxide in the reaction vessel is recycled as carbon dioxide feed for reaction with carbon outside of the vessel and the carbon monoxide generated by reaction of said carbon and carbon dioxide outside of the vessel is cycled to the reaction vessel for conversion into carbon and carbon dioxide.

19. The method as claimed in claim 15 in which minor amounts of carbonates such as limestone are added to the carbonaceous feedstock in order to produce excess carbon dioxide gas to purge air and other volatiles from the entering feedstock material.

20. The method as claimed in claim 15 in which small amounts of oxygen gas are fed into the intensely heated zone of the carbonaceous feedstock in order to produce excess carbondioxide to purge air and other volatiles from the entering feedstock material.

* * * * *